United States Patent [19]

Levin

[11] Patent Number: 5,649,957

[45] Date of Patent: Jul. 22, 1997

[54] ARTICULATED DISSECTOR

[76] Inventor: John M. Levin, 412 Fairview Rd., Narberth, Pa. 19072

[21] Appl. No.: 493,730

[22] Filed: Jun. 22, 1995

[51] Int. Cl.$^6$ .................................................. A61B 17/28
[52] U.S. Cl. ............................................. 606/207; 606/205
[58] Field of Search .................................. 606/205, 207, 606/206, 208, 209; 128/751

[56] References Cited

U.S. PATENT DOCUMENTS

| | | | |
|---|---|---|---|
| 5,235,966 | 8/1993 | Jamner | 606/207 |
| 5,374,277 | 12/1994 | Hassler | 606/207 |
| 5,411,519 | 5/1995 | Tovey et al. | 606/207 |

*Primary Examiner*—Michael Buiz
*Assistant Examiner*—Patrick W. Rasche
*Attorney, Agent, or Firm*—Caesar, Rivise, Bernstein, Cohen & Pokotilow, Ltd.

[57] ABSTRACT

An articulated dissecting surgical tool includes an elongate member having a longitudinal axis and a dissecting tip located at a distal end of the elongate member. The tip includes a pair of opposed jaws and a coupling mechanism pivotally coupling the pair of opposed jaws together at a proximal end of the tip to permit pivotal movement of the opposed jaws relative to each other in a first plane between opened and closed positions. Each of the jaws includes a distal section having a forward and rear end, a proximal section having a forward and rear end, and an articulating pivot connection between the proximal and rear sections. The pivot connection is adjacent the rear end of the distal section and the forward end of the proximal section to permit angular movement of the distal section relative to the proximal section in a second plane different from the first plane to establish a desired angular relationship between the distal and proximal sections of each of the jaws. The rear ends of the proximal sections of the jaws constitute the proximal end of the tip at which the opposed jaws are pivotally coupled.

7 Claims, 1 Drawing Sheet

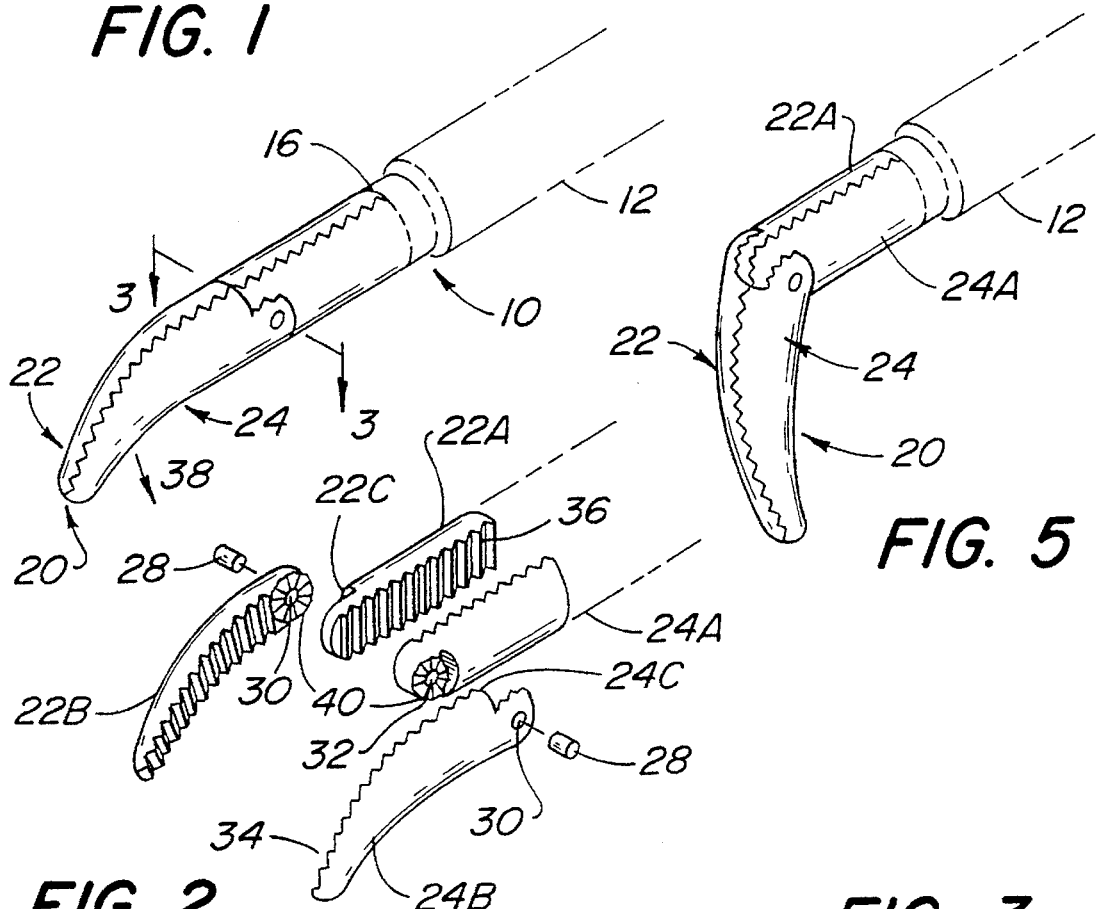
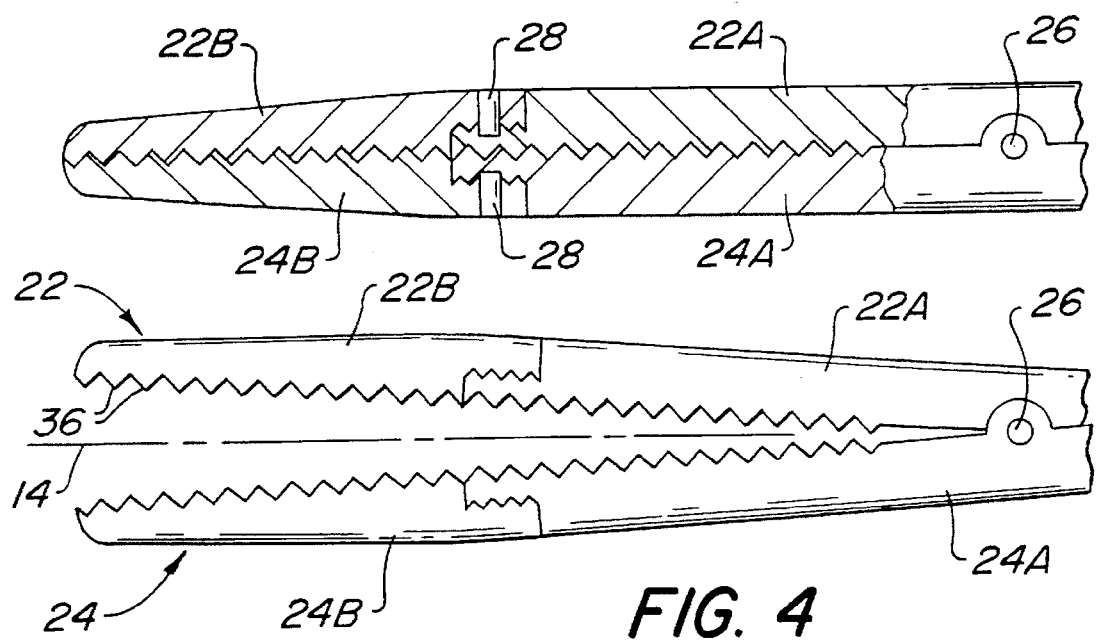

ARTICULATED DISSECTOR

BACKGROUND OF THE INVENTION

This invention relates generally to the field of surgical instruments, and, in particular to a dissector for separating tissue.

Numerous prior art references disclose surgical instruments including dissectors and clamps, wherein the operating end is angled or can be angled with respect to the shaft of the instrument. However, none of the art known to applicant is believed to show or suggest the features of a dissector that can be operated with the tip in a straight direction, and also which can be operated with a forward or distal end of the tip articulated into various angular positions relative to a rear or proximal end of the tip. Prior art devices permit only articulation of the entire operating tip, and usually only at a right angle to the elongate shaft from which the tip extends. The variable articulation of the present invention thereby creates at least two non-collinear working segments that can maintain their cooperation. For example, a variable articulated dissector in accordance with this invention would be able to effectively grip or spread tissue along two non-collinear segments regardless of the angle between the segments. In addition, none of the prior art known to applicant discloses a device which varies the angle between the forward (distal) end and the rear (proximal) end of each jaw forming the tip of the device with relation to the shaft of the dissector by pressing the forward end of the tip against an internal body wall.

For example, in U.S. Pat. No. 5,209,747 (Knoepfler) a surgical instrument with an operating end is disclosed that includes a dissector or a clamp that can be angled with respect to the axis of the shaft of the instrument to a desired angle by rotating a dial. The dial is connected to a rotating shaft, which is coupled to a beveled gear that varies the angle of the entire operating end. The instrument is also capable of providing irrigation, suction and lasing.

U.S. Pat. No. 5,322,505 (Krause, et al.) and U.S. Pat. No. 5,320,635 (Smith, et al.) disclose a surgical cutter with an outer shaft that is curved and a cutting instrument attached to a flexible member within the outer shaft. The angle of the cutting surface is fixed with relation to the axis of the shaft. The instrument facilitates positioning of the cutter without requiring removal from the body and reinsertion but does not provide a variable articulating working head as in the present invention.

U.S. Pat. No. 5,275,608 (Forman, et al.), the entire disclosure of which is incorporated by reference herein, discloses an endoscopic instrument with an operating head member that can be steered within the body by control external to the body cavity, i.e., the angle between the operating member and the shaft of the instrument can be varied, in this case by manipulation of a control member attached to the instrument and external to the body.

Accordingly, a need exists for a dissector which can operate with the tip in a straight direction and which permits the forward or distal end of the tip to be articulated to various angles relative to the proximal end of the tip by pressing the tip against an internal body wall.

SUMMARY OF THE INVENTION

An articulated dissecting surgical tool includes an elongate member having a longitudinal axis and a dissecting tip located at a distal end of the elongate member. The tip includes a pair of opposed jaws and a coupling mechanism pivotally coupling the pair of opposed jaws together at a proximal end of the tip to permit pivotal movement of the opposed jaws relative to each other in a first plane between opened and closed positions. Each of the jaws includes a distal section having a forward and rear end, a proximal section having a forward and rear end, and an articulating pivot connection between the proximal and distal sections. The pivot connection is adjacent the rear end of the distal section and the forward end of the proximal section to permit angular movement of the distal section relative to the proximal section in a second plane different from the first plane to establish a desired angular relationship between the distal and proximal sections of each of the jaws. The rear ends of the proximal sections of the jaws constitute the proximal end of the tip at which the opposed jaws are pivotally coupled.

DESCRIPTION OF THE DRAWINGS

Other objects and many attendant features of this invention will become readily appreciated as the same becomes better understood by reference to the following detailed description when considered in connection with the accompanying drawings wherein:

FIG. 1 is a partial isometric view of the tip of the articulated dissector of the present invention shown in the closed position.

FIG. 2 is a partial exploded isometric view of the tip of the articulated dissector of the present invention.

FIG. 3 is a partial cross-sectional view of the tip of the articulated dissector of the present invention taken along lines 3—3 of FIG. 1.

FIG. 4 is a partial side view of the tip of the articulated dissector of the present invention shown in the open position with the jaws of the tip open in a angled position relative to the longitudinal axis of the dissector.

FIG. 5 is a partial isometric view of the tip of the articulated dissector of the present invention shown with the tip in an articulated position.

DETAILED DESCRIPTION OF THE PREFERRED EMBODIMENT

Referring now to various figures of the drawings where like reference numerals refer to like parts, there is shown at 10 in FIG. 1, a tool constructed in accordance with this invention. The articulated dissecting surgical tool 10 comprises an elongated member 12 having a longitudinal axis 14 as shown in FIG. 4. Extending axially from a distal end 16 of the member 12 is a unique articulated tip 20 for movement in at least two planes through an angle with respect to the longitudinal axis 14.

As shown in FIG. 1, the tip 20 comprises opposed articulated jaws 22 and 24 for dissecting tissue (not shown). In FIG. 4, the jaws 22 and 24 are shown in an open position to engage and dissect tissue. The jaws 22 and 24 are opened by any conventional operating system employing an operating trigger or handle which enables the surgeon to manually open and close the jaws 22 and 24 as desired about a conventional coupling pivot point section 26. For example, such an operating system is shown and described in U.S. Pat. No. 5,275,608 (Forman, et al.), the entire disclosure of which is incorporated by reference herein. Since the specific operating system utilized in the tool 10 is not a limitation on the invention, further discussion of such an operating system is not included herein.

As shown in FIG. 2, each of the jaws 22 and 24 comprise a respective proximal section 22A and 24A, each having a forward and rear end and a respective distal section 22B and 24B, each also having a forward and rear end. The distal sections 22B, 24B of the tip 20 are preferably slightly curved downward from the longitudinal 14 axis as shown in FIG. 1. Each of the forward ends of each of the proximal sections 22A, 24A are hingedly secured at positions 22C, 24C to each of the rear ends of distal sections 22B, 24B at the approximate respective midpoint of each of the jaws 22, 24. It should be readily apparent to those skilled in the art that the articulation of the jaws 22 and 24 at positions 22C, 24C need not occur at the midpoint thereof, but can be located at any point along the length of the jaws 22 and 24 depending upon the circumstances of use. In the embodiment shown in FIG. 2, the opposed proximal sections 22A, 24A are coaxial with the longitudinal axis 14 of the tool 10.

As shown in FIGS. 2 and 3, in hingedly securing each of the opposed proximal sections 22A and 24A to each respective distal section 22B and 24B, a pin 28 extends through a respective hole 30 in each of the opposed proximal sections 22A and 24A at its respective distal end. Each of the pins 28 passes through each respective hole 30 and into a respective pin engaging recess 32 in each of the rear ends of distal sections 22B, 24B. As shown in FIG. 3, the recess 32 does not extend through the entire diameter of each respective opposed proximal sections 22A, 24A.

The pair of opposed jaws 22, 24 are employed to engage tissue (not shown) between the interior surfaces 34 thereof in different linear directions within a plane including the longitudinal axis. The opposed proximal sections 22A and 24A and the opposed distal sections 22B and 24B are non-collinear but each are capable of dissecting tissue (not shown). The interior surfaces 34 of jaws 22, 24 include a plurality of mating tissue engaging teeth 36 that are conventional in the art to enable the gripping and dissecting of tissue, although other types of surfaces, e.g., roughened, sintered, may be utilized depending upon the circumstances of use.

When one wishes to engage tissue (not shown) with the tool 10, the jaws 22 and 24 may be opened and then closed about the tissue by the operating system (not shown) to actuate the jaws 22, 24 about pivot 26 to perform the intended tissue-engagement function. As shown in FIG. 2, the rear end of the proximal sections 22A and 24A of the jaws 22 and 24, constitute the proximal end of the tip 20 at which the opposed jaws 22 and 24 of the tip are pivotally coupled together. When a surgeon utilizes the tool 10 during surgery, the surgeon may articulate the distal sections 22B, 24B of the tip 20 as shown in FIG. 5, about points 22C, 24C, in a downward direction as shown by arrow 38 in FIG. 1 (or upward) from the longitudinal axis 14 by pressing the distal sections 22B, 24B against a body wall or structure (not shown) in which the tool 10 is being utilized. By meeting such resistance in the form of the body wall or structure, the distal sections 22B, 24B will pivot downwardly (or upwardly) about the pins 28. In order to maintain the distal sections 22B, 24B in the desired orientation after such articulation, the proximal sections 22A and 24A are frictionally engaged to the distal sections 22B and 24B by a conventional frictional surface on each mating surface 40 at the articulation point 22C and 24C as shown in FIG. 2. The rear end of each of distal sections 22B and 24B and the forward ends of the proximal sections 22A, 24A are generally thinner than the diameter of the proximal sections 22A, 24A to enable the rear ends of distal sections 22B and 24B to articulatingly mate with the forward ends of proximal sections 22A and 24A and to permit the tip 20 to be of a consistent and smooth surface.

A surgeon can vary the ability of and direction of the tool 10 to engage tissue by articulating the distal sections 22B, 24B of the tip 20 as desired. In order to reverse the direction of the articulation of the distal sections 22B, 24B of the tip 20 from a generally downward to a generally upward direction, the surgeon need merely reverse the action by again pressing the distal sections 22B and 24B against a body structure, in an opposite direction to enable movement of distal sections 22B and 24B about pins 28. This mechanism of articulation facilitates use of the tool 10 since the surgeon can articulate the tip 20 without removing the tool 10 from the body cavity in which the tool 10 is being utilized, thus saving time and effort during surgery.

The dissector of this invention can be used in a conventional manner, in a generally straight or linear orientation of the tip jaws, to spread, grip, and/or tear tissue at or adjacent the front of body parts that need to be isolated as part of a surgical procedure. However, in various situations it is necessary to separate the body part from connecting tissue located behind the body part. For example, in procedures in which it is necessary to place a clamp or ligature on either the cystic duct or artery, it is necessary to get behind that duct or artery to scrape away or tear the connecting areolar tissue therefrom. To accomplish this dissecting operation the tip 20 of the dissecting tool 10 is angled, by manipulating or pivoting the distal sections 22B, 24B of each jaw 22 and 24 relative to their respective connected proximal sections 22A, 24A. Most preferably, each of the distal sections 22B, 24B of each of the jaws 22, 24 is disposed at approximately 90 degrees to its pivotally connected proximal section 22A, 24A, so that the dissecting tip 20 can be wrapped around the cystic duct or artery (not shown) to clean away surrounding and connecting tissue. Once the cystic duct or artery has been separated from the connecting and overlying tissue a clip or ligature can be placed on it if required by the surgical procedure.

Thus, the articulated dissector is extremely versatile; being usable to remove or separate tissue from various portions of body parts.

Without further elaboration the foregoing will so fully illustrate my invention that others may, by applying current or future knowledge, adapt the same for use under various conditions of service.

I claim:

1. An articulated dissecting surgical tool comprising:

an elongate member having a longitudinal axis;

a dissecting tip located at a distal end of the elongate member;

the tip including a pair of opposed jaws and jaw coupling means pivotally coupling the pair of opposed jaws together at a proximal end of the tip for permitting pivotal movement of the opposed jaws relative to each other in a first plane between opened and closed positions, each of the jaws including a distal section having a forward and rear end, a proximal section having a forward and rear end, and an articulating pivot connection between the proximal and distal sections, the pivot connection being adjacent the rear end of the distal section and the forward end of the proximal section for permitting angular movement of the distal section relative to the proximal section in a second plane different from the first plane; and said articulating pivot connection comprising cooperating means between the distal and proximal sections of each of said jaws for establishing and maintaining each of a plurality of desired angular orientations between the distal and proximal sections of each of the jaws for providing a desired dissecting operation, the rear end of the proximal sections of the jaws constituting the proximal end of the tip at which the opposed jaws are pivotally coupled together by the jaw coupling means.

2. The tool of claim 1 wherein the distal and proximal sections of each of the jaws include interior surfaces, the interior surfaces of the distal and proximal sections of one of the pair of jaws mating with cooperating interior surfaces of the distal and proximal sections, respectively, of the other of the pair of jaws when the jaws are in a generally closed position for gripping tissue to be dissected.

3. The tool of claim 2 wherein the cooperating interior surfaces include opposed mating teeth.

4. The tool of claim 1 wherein the tip is curved relative to the longitudinal axis when the distal section and proximal section are disposed at substantially 180 degrees to each other.

5. The tool of claim 1 wherein the articulating pivot connection between the distal section and proximal section of each of the jaws includes a pin.

6. The tool of claim 1 wherein the rear end of the distal section and the forward end of the proximal section of each jaw include cooperating surfaces for aiding in maintaining the distal and proximal sections of each jaw in a desired angular orientation relative to each other during use of the tool in dissecting tissue.

7. A dissecting tip comprising a pair of opposed jaws and jaw coupling means pivotally coupling the pair of opposed jaws together at a proximal end of the tip for permitting pivotal movement of the opposed jaws relative to each other in a first plane between opened and closed positions, each of the jaws including a distal section having a forward and rear end, a proximal section having a forward and rear end, and an articulating pivot connection between the proximal and distal sections, the pivot connection being adjacent the rear end of the distal section and the forward end of the proximal section for permitting angular movement of the distal section relative to the proximal section in a second plane different from the first plane, said articulating pivot connection comprising cooperating means between the distal and proximal sections of each of said jaws for establishing and maintaining each of a plurality of desired angular orientations between the distal and proximal sections of each of the jaws for providing a desired dissecting operation, the rear end of the proximal sections of the jaws constituting the proximal end of the tip at which the opposed jaws are pivotally coupled together by the jaw coupling means.

\* \* \* \* \*